United States Patent [19]

Sawyer

[11] Patent Number: 4,606,910

[45] Date of Patent: Aug. 19, 1986

[54] COMPOSITE HEMOSTATIC ARTICLE INCLUDING A HEMOSTATIC AGENT ONLAY AND METHODS FOR PREPARING THE SAME

[75] Inventor: Philip N. Sawyer, Brooklyn, N.Y.

[73] Assignee: Interface Biomedical Laboratories, Brooklyn, N.Y.

[21] Appl. No.: 625,986

[22] Filed: Jun. 28, 1984

[51] Int. Cl.$^4$ .................... A61L 15/00; A61L 17/00
[52] U.S. Cl. .................... 424/28; 128/156; 128/DIG. 8; 424/15; 514/801
[58] Field of Search .................. 424/28, 15; 514/801; 128/DIG. 8, 156

[56] References Cited

U.S. PATENT DOCUMENTS

| | | | |
|---|---|---|---|
| 4,022,203 | 5/1977 | Ackley | 128/156 |
| 4,233,360 | 11/1980 | Luck et al. | 514/801 |
| 4,238,480 | 12/1980 | Sawyer | 424/177 |
| 4,390,519 | 6/1983 | Sawyer | 424/28 |
| 4,404,970 | 9/1983 | Sawyer | 128/325 |
| 4,407,787 | 10/1983 | Stemberger | 128/156 |
| 4,424,208 | 1/1984 | Wallace et al. | 514/801 |
| 4,453,939 | 6/1984 | Zimmerman et al. | 128/156 |

*Primary Examiner*—Ronald W. Griffin
*Attorney, Agent, or Firm*—Pennie & Edmonds

[57] ABSTRACT

An improved hemostatic article is made by fusing an onlay of hemostatic agent to a porous body which is already impregnated with the same or with a different hemostatic agent. The hemostatic agent(s) may comprise a collagen or collagen-like substance which has been modified by rendering the surface charge thereof effectively more positive than prior to modification.

18 Claims, 8 Drawing Figures

COMPOSITE HEMOSTATIC ARTICLE INCLUDING A HEMOSTATIC AGENT ONLAY AND METHODS FOR PREPARING THE SAME

FIELD OF THE INVENTION

This invention relates to composite hemostatic articles and to methods of preparing the same.

BACKGROUND

In various prior patents, I have shown how certain modifications of collagen, collagen-like compounds and gelatin could augment the hemostatic properties of such compounds by manipulation of the surface charge and microstructure thereof. In U.S. Pat. No. 4,238,480, I disclosed that an improved hemostatic agent could be made by treating collagen or a collagen-like substance to render the surface charge effectively more positive and that the thusly modified substance could be employed to control or terminate bleeding.

Other references relate to the provision of liquid absorbent patches, pads or the like to carry medicaments. For example, in U.S. Pat. No. 4,022,203, Ackley discloses a liquid absorbable pad means containing a quantity of blood coagulating substance to reduce blood flow. In U.S. Pat. Nos. 4,390,519 and 4,404,970, I disclosed that a modified blood-soluble hemostatic agent could be combined with or incorporated into a porous or supporting body such as, for example, a gauze pad, a bandage, a laparotomy pad or a sponge. By embodying the improved hemostatic agent into such porous body, the resulting article itself becomes a hemostatic material possessing the properties of the agent and may be applied to an area of trauma or injury where such properties may be utilized.

I have discovered that there are certain additional advantages which result from the use of such a hemostatic article or material if an onlay of the hemostatic agent can be fused to the surface of an article which has already been impregnated with the agent so that the agent is the first to come in contact with an area of trauma or injury.

SUMMARY OF THE INVENTION

The provision of a coating of a hemostatic agent to a porous body which is already impregnated with the same or a different hemostatic agent will have a number of advantages in clinical application over the hemostatic articles known previously. The different porous materials in which hemostatic agents may be incorporated—gauze, sponge, tissue, etc.—have different absorbencies and different effects on the healing rate of a wound to which the materials may be applied. The provision of a coating of a hemostatic agent which absorbs serum and plasma from an injured area on the surface of such materials will make the effects produced by use of the differing materials more uniform by mitigating any problems which may be encountered in dealing with a particular substrate in clinical use. In addition, if the hemostatic agent coating is more absorbent of serum and plasma from an injured area than is the material which it coats, the provision of such coating has been found to relieve pain in a patient more rapidly than will the material without such coating. For example, a hemostatic agent as disclosed in my U.S. Pat. No. 4,238,480 will have this effect. Further, the provision of a layer of hemostatic agent as a coat on the surface of a hemostatic material can have a comfort effect on a patient by acting as a cushion between the wound and the material.

It is an object of the invention to provide an improved hemostatic article.

It is another object of the invention to provide an improved method for preparing hemostatic articles.

To achieve the above and other objects of the invention, there is provided a method comprising incorporating a first hemostatic agent into a porous body to form a hemostatic material, preparing a second hemostatic agent with at least a portion thereof in liquid phase, affixing an onlay of said second hemostatic agent to said material by freezing the liquid portion of said second hemostatic agent to said material whereby to form an onlaid hemostatic article, and drying the article.

According to one specific embodiment of the invention, the first and second hemostatic agents may be of the same or substantially the same chemical composition. One or both may preferably be prepared by modifying either a collagen or a collagen-like substance in water and modifying the thusly dissolved substance to render the surface charge thereof effectively more positive than prior to modification while retaining the water solubility thereof.

According to a feature of the invention, the hemostatic material is prepared by freezing the first hemostatic agent in the porous body. The porous body may preferably be saturated with said first hemostatic agent.

According to a preferred embodiment of the invention, the second hemostatic agent is prepared with at least a portion thereof in liquid phase by first freezing said second hemostatic agent and then melting at least the surface of the thusly frozen second agent.

According to the invention, there is provided a hemostatic article and an apparatus for producing an improved hemostatic article prepared as indicated above. The apparatus comprises a coating means for applying a liquid layer of a first hemostatic agent to a strip of hemostatic material which comprises a porous body which has been saturated or substantially saturated with either an identical or a different second hemostatic agent, freezing means for fusing a liquid layer of said first hemostatic agent to said hemostatic material, drying means for drying a layer of said first hemostatic agent which has been fused to said hemostatic material, and conveyor means cooperating with said coating, freezing and drying means for furnishing a strip of said hemostatic material to said coating, freezing, and drying means respectively so that a layer of said first agent can be successively applied to said material, fused to said material and dried on said material to form a composite hemostatic article.

DETAILED DESCRIPTION

This disclosure incorporates herein by reference the drawings and disclosures of my prior U.S. Pat. Nos. 4,238,480; 4,390,519 and 4,404,970.

Figure 1:
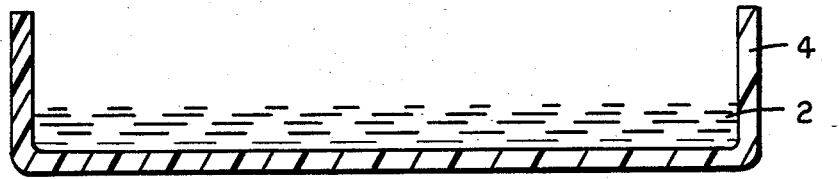
FIGS. 1-6 are schematic representations of a sequence of operations illustrating a method of the invention.

With reference to FIG. 1, a hemostatic agent 2 is placed in a vessel 4 in liquid phase. In accordance with a preferred embodiment of the invention, the hemostatic agent may comprise a collagen substance or a collagen-like substance which has been modified by dissolving the substance in water and modifying the thusly dissolved substance to render the surface charge thereof effectively more positive than prior to modification, in manners which are shown, for example, in my earlier U.S. Pat. No. 4,238,480. Such modified collagen or collagen-like substance may be prepared as taught in said U.S. Pat. No. 4,238,480 and may be freeze dried. The thusly modified and freeze dried hemostatic agent may be dissolved in water for use as the hemostatic agent(s) of the present invention.

Figure 2:
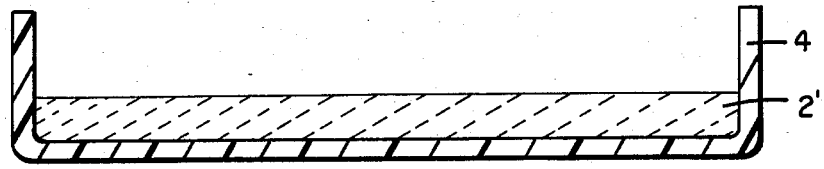

As shown diagrammatically in FIG. 2, the hemostatic agent 2 in the vessel 4 may then be frozen into the solid phase. Reference numeral 2' is used to designate the hemostatic agent in solid, as opposed to liquid, phase.

Figure 3:
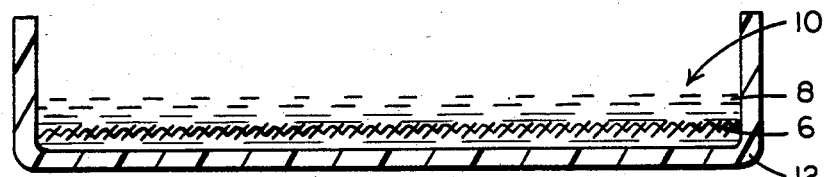

As shown in FIG. 3, a porous body 6 incorporating a hemostatic agent 8 together form a hemostatic material 10 which is placed or prepared in a container 12. The hemostatic agent 8 may be of the same or of substantially the same chemical composition as the hemostatic agent 2 shown in FIG. 1. In other words, the hemostatic agent 8 may be prepared in accordance with the disclosure of, for example, U.S. Pat. No. 4,238,480 by modifying a collagen or collagen-like substance by dissolving it in water and rendering the surface charge thereof effectively more positive than prior to modification. Such hemostatic agent may be incorporated into a porous body such as, for example, a bandage, a small gauze sponge, a pad of surgical gauze, a laparotomy pad, a small sponge of natural or synthetic material or the like as shown, for example, in my earlier U.S. Pat. No. 4,404,970. As shown in the said patent, the hemostatic agent 8 may be incorporated in the porous body by, for example, freezing and drying or vacuum drying the agent in the porous body.

Although lyophilization techniques are known, the following steps may be used relative to the above disclosure:

1. Dispense 50 ml amounts into plastic 100 mm petri dishes.
2. Shelf-freeze in lyophilizer (e.g., Vitrus model 100 SRC-7) at minus 30° to minus 50° C. for 3 to 5 hours, or until eutectic point has been determined.
3. Set condenser for one to two hours; begin vacuum with no heat for three hours.
4. Set shelf heat to plus 30° C. and continue for 48 hours.

Gamma irradiation may be used for sterilization. The following may alternatively be used for sterilization:

1. Place in sterilization envelope and seal with indicator inside.
2. Gas sterilize with ethylene oxide through normal cycle. (Alternatively gamma ray sterilization with Cobalt irradiation to greater than 20 megarads.)
3. Aerate thoroughly following exposure to ethylene oxide.

Figure 4:
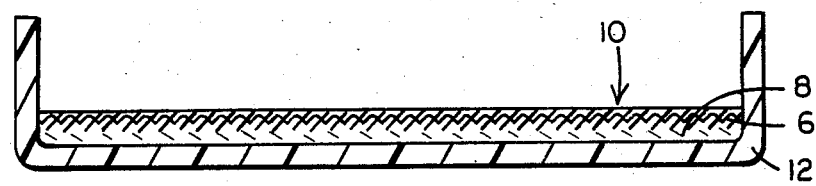

According to a preferred embodiment of the invention, the porous body 6 will be saturated with hemostatic agent 8 in liquid phase. The mixture of liquid hemostatic agent 8 in porous body 6 may then be frozen as illustrated diagrammatically in FIG. 4.

Figure 5:
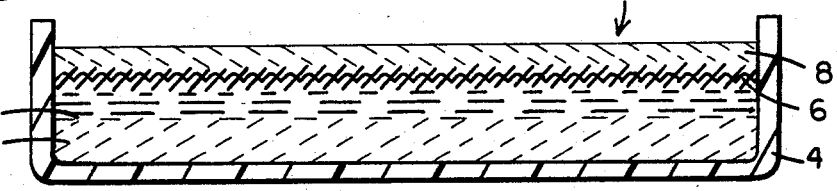
Figure 6:
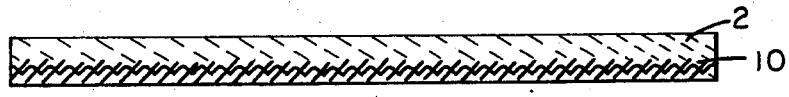

Referring now to FIG. 5, the frozen hemostatic material 10 with hemostatic agent 8 incorporated thereinto is placed on top of frozen hemostatic agent 2' in vessel 4. The surface of hemostatic agent 2' is melted (melted portion designated by reference numeral 2) by methods well known in the art. The hemostatic agent 2' is then fused to the hemostatic material 10 by refreezing the melted portion 2 of hemostatic agent 2' to material 10. The fused hemostatic material-hemostatic agent may then be freeze dried or vacuum dried to remove water from the resultant article. FIG. 6 shows a completed freeze-dried composite article wherein the hemostatic agent 2 has been fused to the face of the hemostatic material 10 and subsequently freeze dried or vacuum dried.

Figure 7:
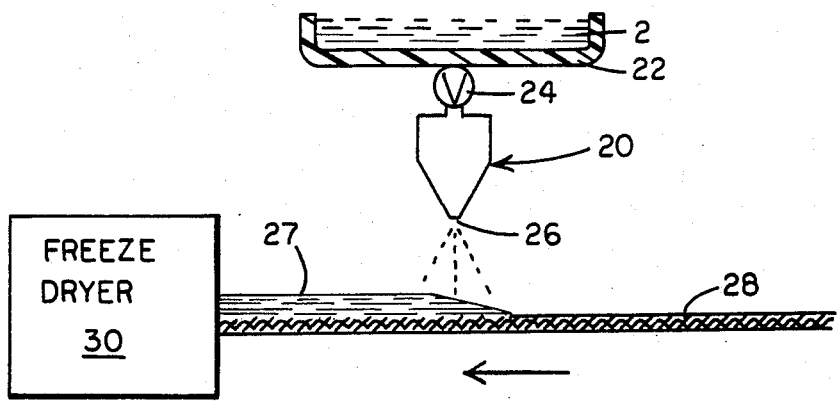
FIG. 7 is a diagramatic view of an apparatus of the invention.

An apparatus for the application of an onlay of hemostatic agent to a continuous strip of hemostatic material in accordance with the principles of the invention will now be described. As shown in FIG. 7, the hemostatic agent 2 can be applied in liquid form to a strip of hemostatic material 28 by means, for example, of a spray applicator, indicated generally at reference numeral 20. Spray applicator 20 comprises a vat 22 containing hemostatic agent 2 in liquid form. In a preferred embodiment of the invention, the hemostatic agent may comprise from 0.25 to 1.5% of an aqueous solution of a collagen or collagen-like substance which has been modified to render the surface charge of such substance effectively more positive than prior to modification in accordance with the teachings of U.S. Pat. No. 4,238,480. The thickness of the onlay preferably is 2-3 mm. The agent 2 is discharged through nozzle 26 to deposit a layer of said agent 27 onto strip 28. Strip 28 comprises an already frozen, saturated mixture of hemostatic agent in, for example, a bandage. This preferably will be prepared in accordance with the teachings of U.S. Pat. Nos. 4,390,519 or 4,404,970. A continuous layer of agent 2 may be deposited onto strip 28 by moving the strip relative to nozzle 26. Valve 24 may be used for regulating the flow of hemostatic agent 2 through nozzle 26. A liquid layer of hemostatic agent 2 which is deposited on strip 28 may then be fused to said strip by passing said strip through a freezer dryer as indicated diagrammatically at 30.

Figure 8:
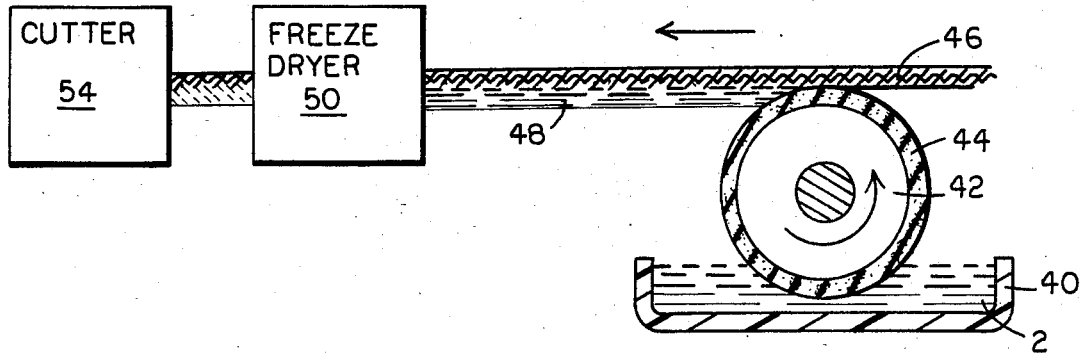
FIG. 8 is a diagramatic view of another apparatus of the invention.

An alternative apparatus for production of a continuous strip of a composite hemostatic article in accordance with the invention is shown in FIG. 8. A strip of hemostatic material 46 comprising a frozen, saturated mixture of a hemostatic agent in a bandage is passed by a rotating cold wheel 42. The wheel is rotated through a vessel 40 containing preferably 0.25 to 1.5% of an aqueous solution of hemostatic agent 2 which, for example, is prepared in accordance with the disclosure of U.S. Pat. No. 4,238,480. The solution may alternatively comprise up to 10% of the agent 2. The wheel comprises a liquid absorbent surface 44 which is a sponge or felt material or the like. The sponge or felt material 44 of the surface picks up hemostatic agent from vessel 40 and brings it into contact with the surface of strip 46 where it is adsorbed by the surface of the frozen material, as shown at 48. The strip of hemostatic material with an adsorbed layer of hemostatic agent is then advanced into a thin mouth, small volume, high energy, freeze dryer, as indicated diagrammatically at 50, to produce a composite bandage in a continuous strip. Cutting means, as indicated diagrammatically at 54, may also be supplied to cut the continuous strip into desired sizes.

There will now be obvious to those skilled in the art many modifications and variations of the above embodiments. These modifications and variations will not depart from the scope of the invention if defined by the following claims.

I claim:

1. A method comprising incorporating a first hemostatic agent into a porous body to form a hemostatic material, preparing a second hemostatic agent with at least a portion thereof in liquid phase, affixing an onlay of said second hemostatic agent to said material by freezing the liquid portion of said second hemostatic agent to said material whereby to form an onlaid hemostatic article, and drying said article.

2. A method as claimed in claim 1 wherein the first and second hemostatic agents are of substantially the same chemical composition.

3. A method as claimed in claim 2 wherein the first and second hemostatic agents are prepared by modifying one of the group consisting of a collagen or a collagen-like substance by dissolving the substance in water and modifying the thusly dissolved substance to render the surface charge thereof effectively more positive than prior to modification while retaining the water solubility of the substance.

4. A method as claimed in claim 3 wherein the second hemostatic agent is incorporated into said porous body in liquid phase and is subsequently frozen thereinto.

5. A method as claimed in claim 4 wherein the porous body is saturated with said first hemostatic agent.

6. A method as claimed in claim 3 wherein the hemostatic material is prepared by freeze drying or vacuum drying the first hemostatic agent in said porous body.

7. A method as claimed in claim 3 wherein the second hemostatic agent is prepared with at least a portion thereof in liquid phase by first freezing said second hemostatic agent and then melting at least the surface of the thusly frozen second agent 8. A method as claimed in claim 1 wherein the onlay of said second hemostatic agent is affixed to said material by rotating a wheel applicator through a vessel containing said second agent and past said material respectively so that a quantity of said second agent is deposited first on said wheel applicator and subsequently on said material with at least a portion thereof in liquid phase, and freezing the liquid portion of said second agent to said material.

9. A method as claimed in claim 8 wherein the liquid portion of said second agent is frozen to said material by passing said material with said second agent deposited thereon into a freezer.

10. A method as claimed in claim 1 wherein the onlay of said second hemostatic agent is affixed to said material by spraying.

11. A method as claimed in claim 1 wherein said article is dried to remove water therefrom.

12. A method for preparing a hemostatic article which comprises:
  incorporating a first hemostatic material into a porous body; and
  affixing a layer or coating of a second hemostatic material upon at least a portion of one surface of said porous body and first hemostatic material.

13. The method of claim 12 wherein the step of affixing a layer or coating of a second hemostatic material comprises applying to said porous body, said second hemostatic material, at least a portion of which is in liquid phase, and drying said liquid phase portion to affix said layer or coating of said second hemostatic agent upon said portion of one surface of said porous body.

14. A hemostatic article prepared in accordance with one of claims 12, 3, 4, 6 or 5.

15. A hemostatic article comprising:
  a porous body;
  a first hemostatic agent incorporated into said porous body; and
  a layer or coating of a second hemostatic agent affixed to at least a portion of one surface of said porous body.

16. The hemostatic article of claim 15 wherein said second hemostatic agent substantially covers said one surface of said porous body.

17. The hemostatic article of claim 15 wherein at least one of said first and second hemostatic agents is a modified collagen or collagen-like substance.

18. The hemostatic article of claim 15 wherein said porous body is a bandage, gauze, pad, strip or sponge, each of a natural or synthetic material.

* * * * *